US009358536B2

(12) United States Patent
Ogawa et al.

(10) Patent No.: US 9,358,536 B2
(45) Date of Patent: Jun. 7, 2016

(54) METHOD FOR PRODUCING AROMATIC HYDROCARBON AND APPARATUS FOR PRODUCING AROMATIC HYDROCARBON (75) Inventors: Yuji Ogawa, Kawagoe (JP); Hongtao Ma, Tokyo (JP)

(73) Assignee: MEIDENSHA CORPORATION, Tokyo (JP)

( * ) Notice: Subject to any disclaimer, the term of this patent is extended or adjusted under 35 U.S.C. 154(b) by 245 days.

(21) Appl. No.: 13/146,272

(22) PCT Filed: Jan. 15, 2010

(86) PCT No.: PCT/JP2010/050377
§ 371 (c)(1),
(2), (4) Date: Jul. 26, 2011

(87) PCT Pub. No.: WO2010/092849
PCT Pub. Date: Aug. 19, 2010

(65) Prior Publication Data
US 2011/0288355 A1    Nov. 24, 2011

(30) Foreign Application Priority Data

Feb. 12, 2009   (JP) ................ 2009-029702

(51) Int. Cl.
*C07C 15/04* (2006.01)
*C07C 2/76* (2006.01)
(Continued)

(52) U.S. Cl.
CPC *B01J 38/10* (2013.01); *B01J 29/48* (2013.01); *B01J 29/90* (2013.01); *C07C 2/76* (2013.01); *C10G 45/68* (2013.01); *C10G 45/70* (2013.01);
(Continued)

(58) Field of Classification Search
CPC ...... C07C 15/04; C07C 2/76; C07C 2529/40; B01J 29/40; B01J 2229/42
USPC ......................... 585/415, 407, 400
See application file for complete search history.

(56) References Cited

U.S. PATENT DOCUMENTS

2008/0249342 A1* 10/2008 Iaccino et al. ................ 585/402

FOREIGN PATENT DOCUMENTS

EP    0 493 040 A2    7/1992
JP    5-58919 A    3/1993
(Continued)

OTHER PUBLICATIONS

JP 2004269398_ENG—Machine translated English document.*
(Continued)

*Primary Examiner* — In Suk Bullock
*Assistant Examiner* — Youngsul Jeong
(74) *Attorney, Agent, or Firm* — Foley & Lardner LLP (57) ABSTRACT To economically regenerate a catalyst and to produce aromatic hydrocarbon stably for a long time maintaining a high aromatic hydrocarbon yield when the aromatic hydrocarbon is produced upon making a contact reaction between lower hydrocarbon and the catalyst.
A method of producing aromatic hydrocarbon and an apparatus for producing aromatic hydrocarbon by repeating a reaction step for obtaining aromatic hydrocarbon upon making a contact reaction between lower hydrocarbon and a catalyst and a regeneration step for regenerating the catalyst used in the reaction step. Off-gas which is gas obtained by removing aromatic hydrocarbon produced in the reaction step from discharge gas passing through the reaction step is used as a regeneration gas in the regeneration step.

3 Claims, 5 Drawing Sheets (51) Int. Cl.
*B01J 38/10* (2006.01)
*B01J 29/48* (2006.01)
*B01J 29/90* (2006.01)
*C10G 45/68* (2006.01)
*C10G 45/70* (2006.01)
*C10G 45/72* (2006.01)

(52) U.S. Cl.
CPC ............. *C10G 45/72* (2013.01); *B01J 2229/32* (2013.01); *B01J 2229/42* (2013.01); *C07C 2529/40* (2013.01); *C07C 2529/70* (2013.01); *C10G 2400/30* (2013.01); *Y02P 20/52* (2015.11); *Y02P 20/584* (2015.11)

(56) References Cited

FOREIGN PATENT DOCUMENTS

| JP | 2001-334152 A |  | 12/2001 |
| JP | 2003-26613 A | * | 1/2003 |
| JP | 2003-26613 A |  | 1/2003 |
| JP | 2004-269398 A |  | 9/2004 |
| JP | 2004269398 A | * | 9/2004 |
| JP | 2005-343879 A |  | 12/2005 |
| JP | 3985038 A |  | 10/2007 |
| JP | 2008-266244 A | * | 11/2008 |

OTHER PUBLICATIONS

Machine translated paptent application of JP2008-266244 A (English).*
Machine-translated English document of JP2003-26613A.*
Solymosi, F. et al., "Aromatization of Methane over Supported and Unsupported Mo-Based Catalysts", *Journal of Catalysis*, vol. 165, pp. 150-161, (1997).
U.S. Appl. No. 13/146,274, filed Jul. 26, 2011, Ma.

* cited by examiner

FIG.10

METHOD FOR PRODUCING AROMATIC HYDROCARBON AND APPARATUS FOR PRODUCING AROMATIC HYDROCARBON

TECHNICAL FIELD

This invention relates to a method of effectively producing aromatic compound such as benzene or the like and hydrogen from lower hydrocarbon such as methane, ethane, propane and/or the like, and particularly to the method of effectively producing aromatic compound such as benzene or the like from lower hydrocarbon by using a catalyst.

BACKGROUND ART

Hitherto aromatic compound such as benzene, toluene, xylene or the like is produced mainly from naphtha. As production methods for naphthalenes, a non-catalyst method such as a solvent extraction process for coal or the like and a gas thermal cracking process for natural gas, acetylene or the like are employed.

However, according to these conventional methods, only several percents of benzene or naphthalenes can be obtained relative to a raw material such as coal, acetylene or the like. Additionally, much by-product aromatic compounds and hydrocarbons, tar and insoluble carbon residues are produced, which offers problems. Additionally, there is such a drawback that the solvent extraction process for coal or the like requires much organic solvent.

As a method of producing aromatic hydrocarbon such as benzene, naphthalene or the like and hydrogen from lower hydrocarbon, particularly methane, a method of reacting methane in presence of a catalyst or in absence of oxygen or an oxidizing agent is known (see, for example, Non-patent Citation 1). As the catalyst in this case, molybdenum carried on ZSM-5 is assumed to be effective. However, in case of using the catalyst, there are such problems to be solved that a catalytic activity is remarkably lowered owing to carbon deposition, and a methane conversion rate is low.

As a measure for solving the above problems, Patent Citation 1 discloses a method for producing aromatic compound and hydrogen from lower hydrocarbon such as methane, ethane or the like, in which $CO_2$ or CO is added to a gas to be reacted thereby suppressing carbon deposition as a side reaction thus stably producing aromatic hydrocarbon such as benzene or the like for a long time, while suppressing a catalytic activity lowering due to a reaction. Patent Citation 2 discloses that hydrogen is added to a raw material gas thereby stably carrying out a catalytic reaction for a long time. Additionally, Patent Citation 3 discloses that a contact reaction for producing aromatic hydrocarbon from lower hydrocarbon and a catalyst regeneration reaction for regenerating a deteriorated catalyst are alternately repeated thereby stably producing aromatic hydrocarbon and hydrogen.

PRIOR ART CITATION

Patent Citation

Patent Citation 1: Japanese Patent Provisional Publication No. 2001-334152
Patent Citation 2: Japanese Patent Provisional Publication No. 2004-269398
Patent Citation 3; Japanese Patent No. 3985038

NON-PATENT CITATION

Non-patent Citation 1: JOURNAL OF CATALYSIS, 1997, Volume 165, p. 150-161

DISCLOSURE OF THE INVENTION

Problems to be Solved by the Invention

With the method as disclosed in Patent Citation 1, the yield of aromatic hydrocarbon is high when the concentration of carbon dioxide or the like to be added is low; however, an operation-possible time becomes very short because a lowering in catalytic activity is remarkable owing to coking. Additionally, if the concentration of carbon dioxide to be added is made high, coking can be suppressed while prolonging the operation-possible time; however, there is such a problem that an aromatization reaction is impeded with hydrogen which is generated owing to excessive carbon dioxide and methane as a raw material, thereby largely lowering the yield of aromatic hydrocarbon.

Additionally, Patent Citation 3 discloses using hydrogen as a regeneration gas. Hydrogen recovered from a gas produced in a catalytic reaction is used as a regeneration gas; however, a high concentration of hydrogen is used for the regeneration, and therefore hydrogen gas must be supplemented from the outside of a system so as to be economically disadvantageous.

Accordingly, an object of the present invention is to provide a method for producing aromatic hydrocarbon upon making a contact reaction between lower hydrocarbon and a catalyst, in which the catalyst can be economically regenerated while producing aromatic hydrocarbon for a long time maintaining the yield of aromatic hydrocarbon high.

A method of producing aromatic hydrocarbon, according to the present invention, to attain the above object comprises repeating a reaction step for obtaining aromatic hydrocarbon upon making a contact reaction between lower hydrocarbon and a catalyst and a regeneration step for regenerating the catalyst used in the reaction step, which is characterized in that off-gas which is gas obtained by removing aromatic hydrocarbon produced in the reaction step from discharge gas passing through the reaction step is used as a regeneration gas in the regeneration step.

In the above aromatic hydrocarbon producing method, the reaction step may be changed over into the regeneration step, based on a hydrogen concentration in the off-gas.

Additionally, in the above aromatic hydrocarbon producing method, the reaction step may be changed over into the regeneration step, based on a condition in which a hydrogen concentration in the off-gas is not lower than 15%.

A system for producing aromatic hydrocarbon according to the present invention to attain the above-mentioned object is characterized by comprising: a reactor in which a reaction step for obtaining aromatic hydrocarbon upon making a contact reaction between lower hydrocarbon and a catalyst and a regeneration step for regenerating the catalyst used in the reaction step are repeated; and aromatic hydrocarbon separation means for separating aromatic hydrocarbon produced in the reaction step from gas discharged from the reactor, wherein off-gas which is gas obtained by removing aromatic hydrocarbon produced in the reaction step from discharge gas passing through the reaction step is used as a regeneration gas in the regeneration step.

In the above aromatic hydrocarbon producing system, the reactor may includes a plurality of reactors, wherein the reaction step may be carried out by at least one reactor, wherein the off-gas in the reaction step may be supplied to another reactor to carry out the regeneration step.

Effects of the Invention

According to the above invention, when aromatic hydrocarbon is produced by reacting lower hydrocarbon and the catalyst, the catalyst can be economically regenerated while aromatic hydrocarbon can be produced stably for a long time maintaining a high aromatic hydrocarbon yield.

BRIEF DESCRIPTION OF THE DRAWINGS

FIG. 7 including (a) which is a diagrammatic view of the aromatic hydrocarbon producing system according to a second embodiment of the present invention (in case that a catalytic reaction is carried out in the first reactor), and (b) which is a diagrammatic view of the aromatic hydrocarbon producing system according to the second embodiment of the present invention (in case that a regeneration reaction is carried out in the first reactor);

MODE FOR CARRYING OUT THE INVENTION

This invention relates to a method of producing aromatic hydrocarbon upon making a reaction of lower hydrocarbon in presence of a catalyst, which is characterized by adding carbon dioxide in an amount smaller than an excessive amount during the reaction and by regenerating the catalyst by substituting a reaction gas with a regeneration gas every a certain time.

The present invention is characterized particularly by supplying a gas (hereinafter referred to as off-gas) which is obtained by separating produced aromatic hydrocarbon from a gas obtained after the catalytic reaction, in the regeneration step.

By using the gas obtained after the above-mentioned catalytic reaction as the regeneration gas in the regeneration step, it is possible that a plurality of stages (for example, m stages: m is an integer) of catalytic reaction layers are provided, in which the catalytic reaction is made at n stage (n is an integer, and n<m), and gas discharged at the n stage is used as the regeneration gas for n+1 stage so as to make a regeneration reaction.

In other words, it is made possible to continuously carry out the catalytic reaction and the regeneration reaction while suppressing a remarkable carbon (coke) deposition by adding carbon dioxide in the amount smaller than the excessive amount. Additionally, the reaction can be made for a long time maintaining a high yield without accumulation of removal-difficult coke by making the catalytic reaction by substituting the reaction gas with the regeneration gas every a certain time.

A zeolite-based catalyst to be used as the catalyst in the present invention is not particularly limited if it is a zeolite catalyst having a catalytic activity. As the zeolite-based catalyst, for example, zeolite-based catalysts such as mordenite; erionite; ferrierite; "ZSM-5", "ZSM-4", "ZSM-8", "ZSM-11", "ZSM-12", "ZSM-20", "ZSM-40", "ZSM-35" and/or "ZSM-48" commercially available from Mobil Oil Corporation; and/or the like can be used. Additionally, as the zeolite-based catalyst, known zeolite-based catalysts, for example, crystalline aluminosilicate including so-called meso-porous zeolite and/or the like such as "MCM-41", "MCM-48", "MCM-50", "FSM-41", "M41S" and/or the like; different element-containing zeolite such as porosilicate, gallosilicate, ferroaluminosilicate, titanosilicate, and/or the like; and/or the like can be used. Of these zeolite-based catalysts, those suitable for a hydration reaction for olefin are crystalline aluminosilicate and gallosilicate having a pentasil structure.

As the zeolite-based catalyst, that of the proton exchange type (H-type) is usually used. Additionally, a part of protons in the zeolite-based catalyst may be substituted with at least one kind selected from alkali metal such as Na, K, Li and the like, alkaline earth element such as Mg, Ca, Sr and the like, transition metal element such as Fe, Co, Ni, Ru, Pd, Pt, Zr, Ti and the like. Additionally, the zeolite-based catalyst may contain Ti, Zr, Hf, Cr, Mo, W, Th, Cu, Ag and/or the like in a suitable amount.

The zeolite-based catalyst is not particularly restricted in its state and may be used in any state such as powdery state, granular state and the like. Additionally, alumina, titania, silica, clayey compound and/or the like may be used as a carrier or a binder for the zeolite-based catalyst.

The zeolite-based catalyst may be used upon being formed into pellet or extruded product by adding a binder such as silica, alumina, clay and/or the like to it.

In the present invention, lower hydrocarbon means a mixture containing methane in an amount of at least 50% and preferably not less than 70% and additionally containing saturated and unsaturated hydrocarbons having a carbon number of 2 to 6. Examples of these saturated and unsaturated hydrocarbons having a carbon number of 2 to 6 are ethane, propane, propylene, n-butane, isobutane, n-butene, isobutene and the like.

An aromatization reaction for lower hydrocarbon in the method of producing aromatic hydrocarbon and hydrogen from lower hydrocarbon according to the present invention can be accomplished by a reaction-mode such as a batch-mode or a flow-mode. Particularly, it is preferable to accomplish the reaction by the flow-mode using a fixed bed, a moving bed, a fluidized bed, or the like.

A temperature of the reaction is 300° C. to 900° C., preferably 450° C. to 800° C., and a pressure of the reaction is 0.01 MPa to 1 MPa, preferably 0.1 MPa to 0.7 MPa.

(First Embodiment)

Figure 1:
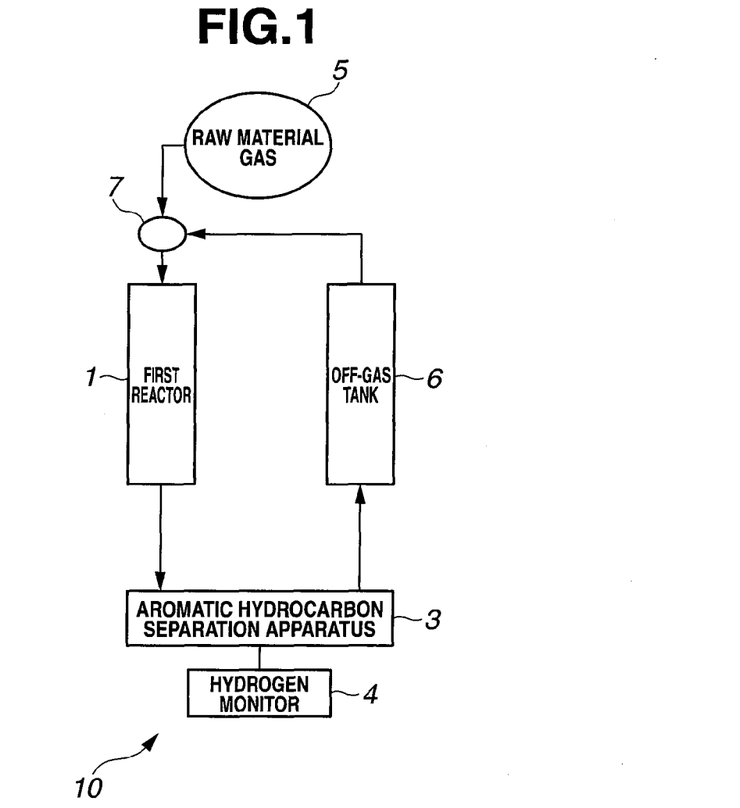
FIG. 1 is a diagrammatic view of an aromatic hydrocarbon producing system according to a first embodiment of the present invention.

Here, the aromatic hydrocarbon producing apparatus according to a first embodiment of the present invention will be discussed with reference to FIG. 1. As shown in FIG. 1, the aromatic hydrocarbon producing apparatus 10 according to the first embodiment of the present invention is constituted of a first reactor 1, an aromatic hydrocarbon separation apparatus 3, a hydrogen monitor 4, an off-gas tank 6, a raw material gas tank 5, and a valve 7.

The first reactor 1 is charged with a catalyst for aromatizing lower hydrocarbon. A raw material gas (for example, methane) is supplied from the raw material gas tank 5 and makes a contact reaction with the catalyst, thereby producing aromatic hydrocarbon (for example, benzene) and hydrogen.

Gas obtained after a catalytic reaction and discharged from the first reactor 1 is supplied to the aromatic hydrocarbon separation apparatus 3 which separates aromatic hydrocarbon produced in the first reactor 1, from the supplied gas.

As a means for separating aromatic hydrocarbon, a cooling separating means for recovering aromatic hydrocarbon by cooling the gas, a means for recovering organic components by passing the gas through an absorbing liquid, and a means using a separation membrane are proposed and applicable.

The hydrogen monitor 4 detects a hydrogen concentration in the off-gas in the aromatic hydrocarbon separation apparatus 3.

Additionally, the off-gas is supplied from the off-gas tank 6 to the first reactor 1 thereby also making a regeneration reaction for the catalyst in the first reactor 1.

Discussion will be made on a method of producing aromatic hydrocarbon upon carrying out a catalytic reaction in the aromatic hydrocarbon producing system 10 according to the first embodiment of the present invention.

When a changeover action of a valve 7 is made to supply the raw material gas (for example, gas containing methane) from the raw material gas tank 5 to the first reactor 1, methane reacts with the catalyst in the first reactor 1 to produce aromatic hydrocarbon (for example, benzene) and hydrogen.

Thus produced benzene and hydrogen (containing unreacted methane and argon and the like in a reaction gas) are supplied to the aromatic hydrocarbon separation apparatus 3 in which aromatic hydrocarbon is separated and removed. Gas (off-gas) obtained upon removing aromatic hydrocarbon from discharge gas obtained after the reaction is stored in the off-gas tank 6.

At this time, a hydrogen concentration of the off-gas is measured by the hydrogen monitor 4 provided to the aromatic hydrocarbon separation apparatus 3. The hydrogen concentration is a standard for making a changeover between the catalytic reaction and the regeneration reaction in the first reactor 1, which will be discussed in detail after.

Next, discussion will be made on a method for carrying out the regeneration reaction in the aromatic hydrocarbon producing system 10 according to the first embodiment of the present invention.

When a changeover action of the valve 7 is made to supply the off-gas in the off-gas tank 6 into the first reactor 1, the catalyst charged in the first reactor 1 is regenerated with hydrogen in the off-gas.

When the catalyst is regenerated, a changeover action of the valve 7 is again made to supply the raw material gas into the first reactor 1 so as to make the catalytic reaction.

Thus, by repeating the catalytic reaction and the regeneration reaction, production of aromatic hydrocarbon can be accomplished at a high yield for a long time.

Hereinafter, discussion will be made in detail on the aromatic hydrocarbon producing system according to the first embodiment of the present invention with reference to examples.

A lower hydrocarbon aromatization catalyst (hereafter referred to as catalyst) was prepared by a preparation method as discussed below, using H-type ZSM-5 zeolite ($SiO_2$/$Al_2O_3$=40) as a metallosilicate carrier.

400 g of HZSM-5 subjected to a silane treatment was dissolved in an aqueous solution prepared by dissolving certain amounts (the mol ratio between molybdenum and zinc is 10:3) of ammonium molybdate and zinc nitrate into 2000 ml of ion-exchanged water, and stirring was made at room temperature for 3 hours so that zinc and molybdenum were carried on HZSM-5.

After the obtained ZSM carrying zinc and molybdenum (Zn(1.23 wt %)/Mo (6 wt %)/HZSM-5) was dried, it was calcined at 550° C. for 8 hours thereby obtaining catalyst powder. Further, 15 parts of an inorganic binder was added to 85 parts of this catalyst powder, and then an extrusion formation into the pellet state was made, followed by calcination, thereby producing a catalyst.

By charging the first reactor 1 of the reaction system 10 in FIG. 1 with the obtained catalyst, a test for producing aromatic hydrocarbon from lower hydrocarbon was conducted. Evaluation of the catalyst was accomplished with the yield of benzene relative to lower hydrocarbon which was flown through. The yield of benzene was defined as indicated below.

Benzene yield (%)={(quantity of benzene produced (mol))/(quantity of methane supplied for a methane reforming reaction(mol))}×100

Hereinafter, common reaction conditions in each test are shown below.

Reaction temperature: 780° C.;
Pressure: 0.15 MPa;
Weight hourly space velocity (WHSV): 30000 ml/g-MFI/h; and
Composition of the reaction gas: methane (89%), argon (9.9%) and carbon dioxide (1.1%)

A pretreatment for the catalyst was conducted as follows: The temperature of the catalyst was raised to 550° C. in the stream of air and kept for 2 hours. Thereafter, air was substituted with a pretreatment gas containing 20% of methane and 80% of hydrogen, and the temperature of the catalyst was raised to 700° C. and kept for 3 hours. Thereafter, the pretreatment gas was substituted with the above-mentioned reaction gas, and the temperature of the catalyst was raised to a certain temperature (780° C.) thus accomplishing the evaluation of the catalyst.

Hydrogen, argon and methane were analyzed by TCD-GC, while aromatic hydrocarbons such as benzene, toluene, xylene and naphthalene and the like were analyzed by FID-GC.

Figure 2:
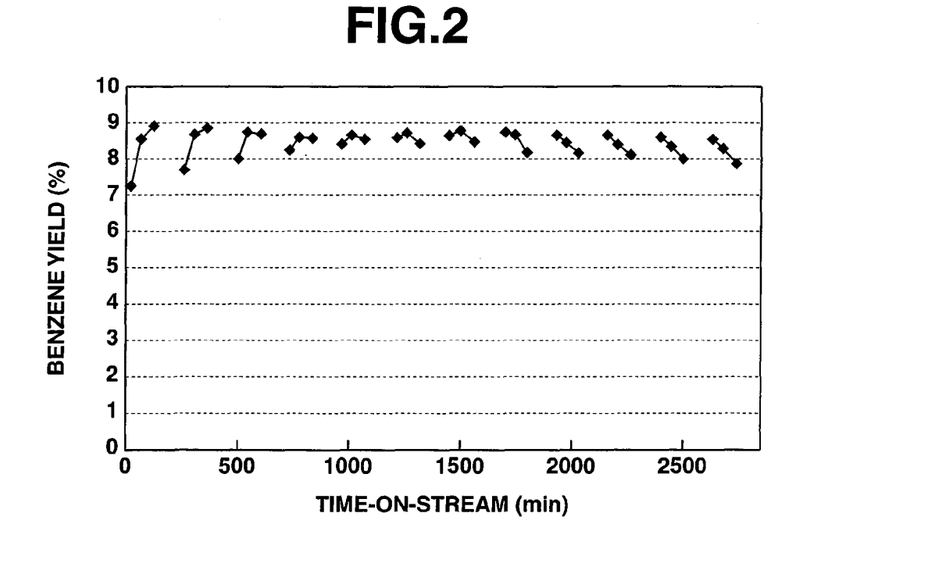
FIG. 2 is a graph showing a time-based change of a benzene yield obtained when a catalytic reaction and a regeneration reaction are repeated in the aromatic hydrocarbon producing system according to the first embodiment of the present invention.
Figure 3:
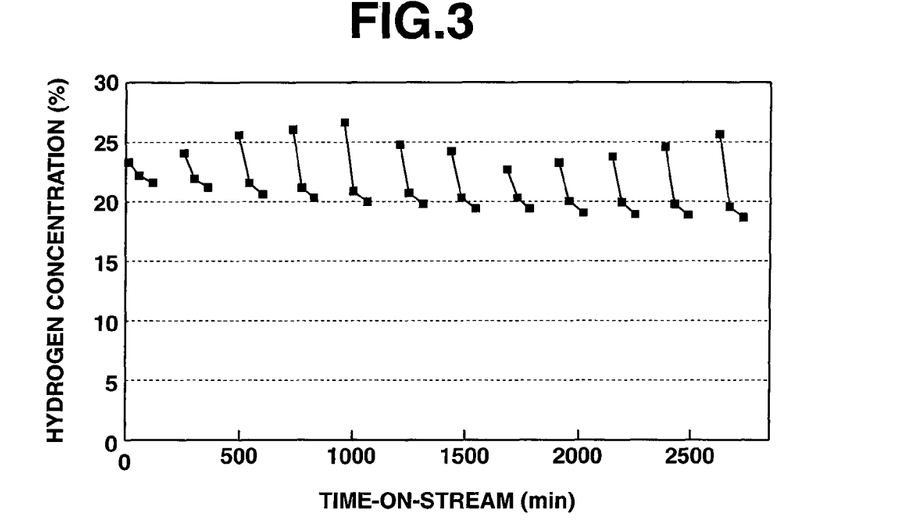
FIG. 3 is a graph showing a time-based change of a hydrogen concentration in off-gas in a first reactor, obtained when aromatic hydrocarbon is produced in the aromatic hydrocarbon producing system according to the first embodiment of the present invention.

FIGS. 2 and 3 show analysis results in benzene yield and hydrogen concentration obtained when production of aromatic hydrocarbon and regeneration of the catalyst were carried out by repeating a cycle including 2 hours of the catalytic reaction and 2 hours of the reaction for regenerating the catalyst after the catalytic reaction in the aromatic hydrocarbon producing system 10.

As shown in FIG. 2, it was confirmed that the regeneration of the catalyst could be made with the off-gas so that the catalyst could be used for a long time.

From the results in FIG. 3, it was understood that the hydrogen concentration of the off-gas in the first reactor 1 lowered by making the catalytic reaction. Additionally, it was confirmed that the above-mentioned hydrogen concentration rose after the regeneration reaction.

In the above examples, the hydrogen concentration of the off-gas in the first reactor 1 during the reaction varied within a range between not lower than 15% and not higher than 25%. Accordingly, a control for making a changeover from the catalytic reaction to the regeneration reaction can be carried out watching the hydrogen concentration to prevent the hydrogen concentration from becoming not higher than 15%, in place of making the changeover from the catalytic reaction to the regeneration reaction every a certain time.

Figure 4:
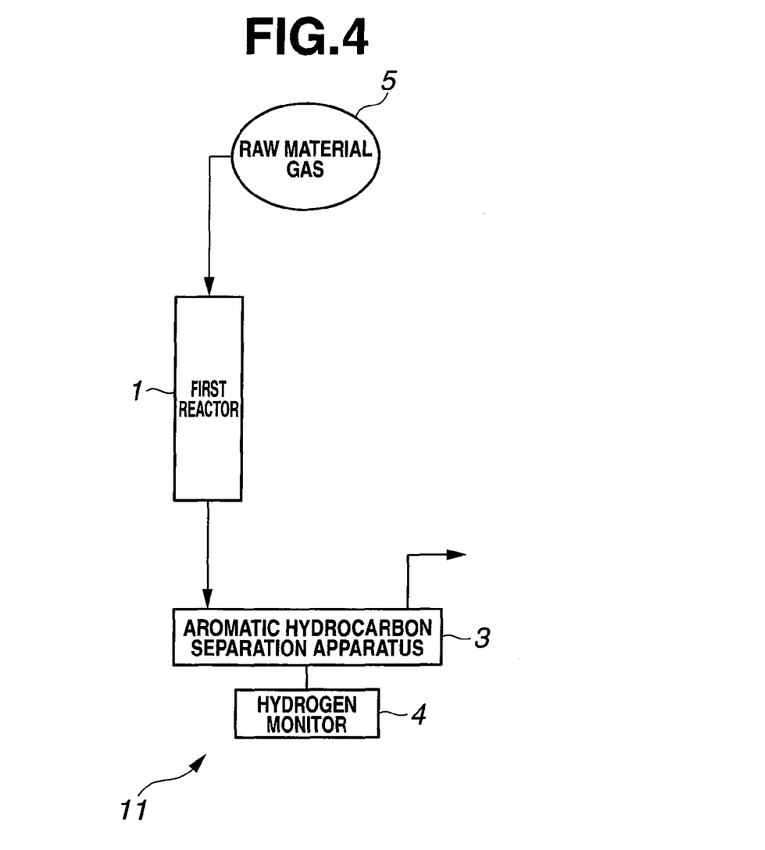
FIG. 4 is a diagrammatic view of an aromatic hydrocarbon producing system as a comparative example relative to the present invention.

In this regard, an aromatization reaction for lower hydrocarbon was carried out in an aromatic hydrocarbon producing system 11 shown as a comparative example in FIG. 4, in which a hydrogen concentration in off-gas and deterioration of a catalyst were studied. In the aromatic hydrocarbon producing system 11 in FIG. 4, the same reference numerals are assigned to the same parts and elements as those in the aromatic hydrocarbon producing system 10 shown in FIG. 1 thereby omitting detailed explanations thereof.

Figure 5:
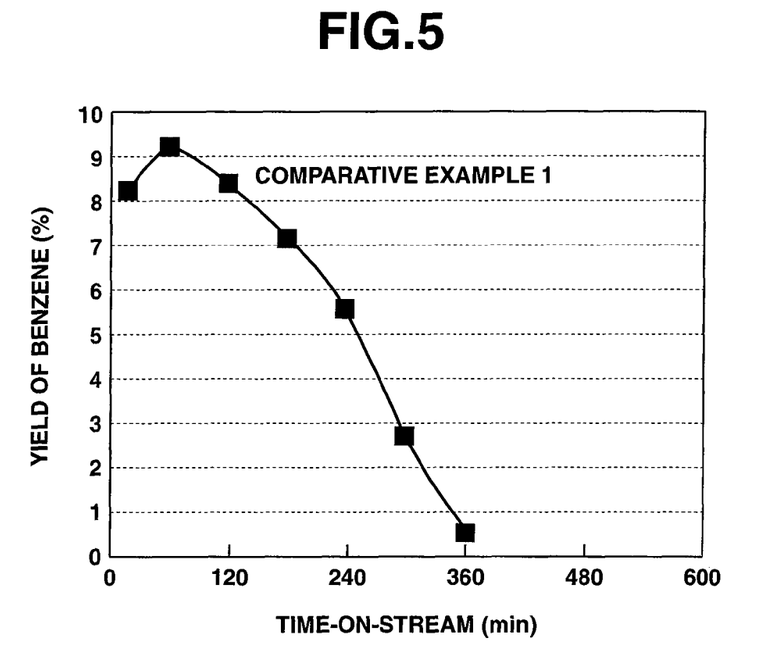
FIG. 5 is a graph showing a time-based change of a benzene yield in case that a catalytic reaction is continuously carried out in the aromatic hydrocarbon producing system as the comparative example relative to the present invention.

FIG. 5 shows a time lapse-based change of a benzene yield obtained when a contact reaction between lower hydrocarbon and the catalyst was continuously made without carrying out the regeneration reaction. Additionally, FIG. 6 shows a time lapse-based change of a hydrogen concentration in the off-gas, obtained when a contact reaction between lower hydrocarbon and the catalyst was continuously made without carrying out the regeneration reaction.

Figure 6:
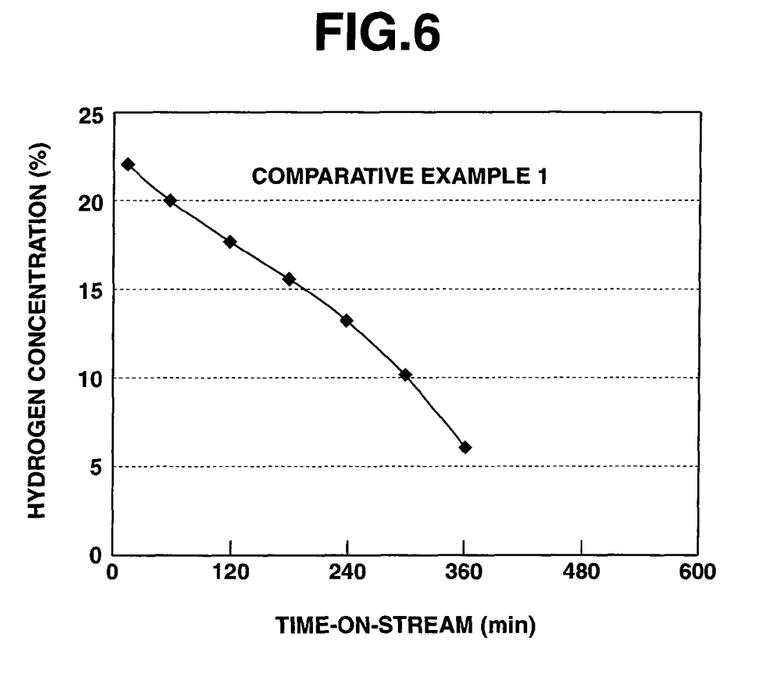
FIG. 6 is a graph showing a time-based change of a hydrogen concentration in off-gas in case that a catalytic reaction is continuously carried out in the aromatic hydrocarbon producing system as the comparative example relative to the present invention.

Comparison between FIG. 5 and FIG. 6 shows the fact that there is a correlation between the benzene yield and the hydrogen concentration in the off-gas. Lowering in benzene yield indicates that the deterioration of the catalyst proceeds. Particularly when the hydrogen concentration is not higher than 15%, the benzene yield is also low, so that the deterioration of the catalyst proceeds while forming a corking section which cannot be removed.

(Second Embodiment)

Figure 7:
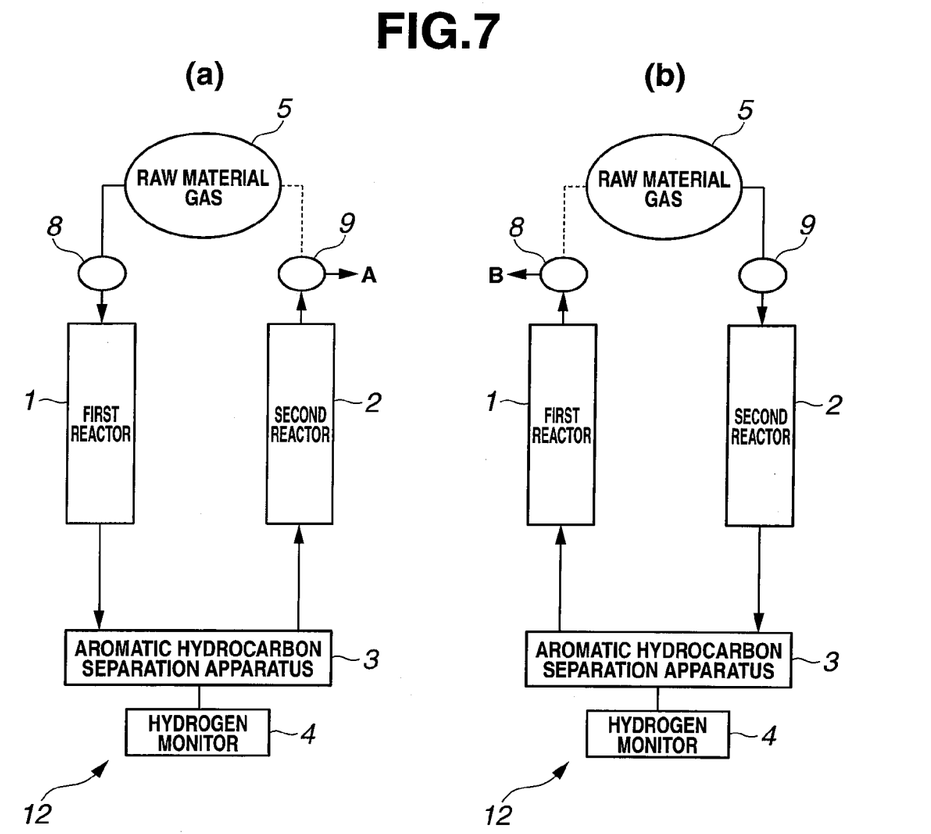

FIG. 7 shows the aromatic hydrocarbon producing system according to a second embodiment of the present invention. The same reference numerals are assigned to the same parts and elements as those of the aromatic hydrocarbon producing system of FIG. 1 thereby omitting the detailed explanation thereof.

The aromatic hydrocarbon producing system according to the second embodiment of the present invention is featured by being provided with a first reactor 1 and a second reactor 2. By being provided with two reactors, gas obtained after the reaction and discharged from one of the reactors can be supplied as a regeneration gas to the other reactor.

Discussion will be made on a method of producing aromatic hydrocarbon in the aromatic hydrocarbon producing system 12 according to the second embodiment of the present invention.

As shown at (a) in FIG. 7, the catalytic reaction is carried out in the first reactor 1.

A changeover action of a valve 8 is made to supply raw material gas from the raw material gas tank 5 to the first reactor 1, and a changeover action of a valve 9 is made to discharge gas obtained after the regeneration reaction and discharged from the second reactor 2 to the outside of the system.

In the first reactor 1 which is charged with the catalyst for aromatizing lower hydrocarbon, aromatic hydrocarbon such as benzene and/or the like is produced from the reaction gas (lower hydrocarbon) supplied thereto.

Discharge gas from the first reactor 1 is sent to the aromatic hydrocarbon separation apparatus 3 in which aromatic hydrocarbon produced in the first reactor 1 is separated and removed.

Gas (off-gas) discharged from the aromatic hydrocarbon separation apparatus 3 is supplied to the second reactor 2. In the second reactor 2, regeneration of the lower hydrocarbon aromatizing catalyst charged in the second reactor 2 is carried out with hydrogen contained in the off-gas.

After making the reaction for producing aromatic hydrocarbon, the regeneration reaction inside the first reactor 1 is carried out. The regeneration reaction of the catalyst inside the first reactor 1 will be discussed with reference to (b) in FIG. 7.

As shown at (b) in FIG. 7, a changeover action of the valve 9 is made to supply raw material gas from the raw material gas tank 5 to the second reactor 2, and a changeover action of the valve 8 is made to discharge gas obtained after the regeneration reaction and discharged from the first reactor 1 to the outside of the system.

In the second reactor 2 which is charged with the catalyst for aromatizing lower hydrocarbon, aromatic hydrocarbon such as benzene and/or the like is produced from lower hydrocarbon supplied thereto. Discharge gas from the second reactor 2 is sent to the aromatic hydrocarbon separation apparatus 3 in which aromatic hydrocarbon produced in the second reactor 2 is separated and removed.

Gas (off-gas) discharged from the aromatic hydrocarbon separation apparatus 3 is supplied to the first reactor 1. In the first reactor 1, regeneration of the lower hydrocarbon aromatizing catalyst charged in the first reactor 1 is carried out with hydrogen contained in the off-gas.

Thus, the two reactors are connected such that the raw material gas and the regeneration gas are alternately flown through each of them, in which aromatic hydrocarbon such as benzene and/or the like can be produced continuously and effectively in the aromatic hydrocarbon producing system 12. Further, not less than two reactors may be provided in the system, and an economical producing system can be realized because the reaction can be made upon carrying out the regeneration of the catalyst in the reactor with the off-gas generated under the catalytic reaction without using a particular generation gas.

The aromatic hydrocarbon producing system 12 according to the second embodiment of the present invention will be specifically discussed with reference to examples.

Preparing conditions of the catalyst, reaction conditions, analysis methods and the like are the same as those in the examples in the first embodiment, and therefore explanation of those will be omitted.

The first reactor 1 and the second reactor 2 as shown in FIG. 7 were charged with the catalyst for aromatizing lower hydrocarbon, thereby carrying out the reaction for producing aromatic hydrocarbon.

Figure 8:
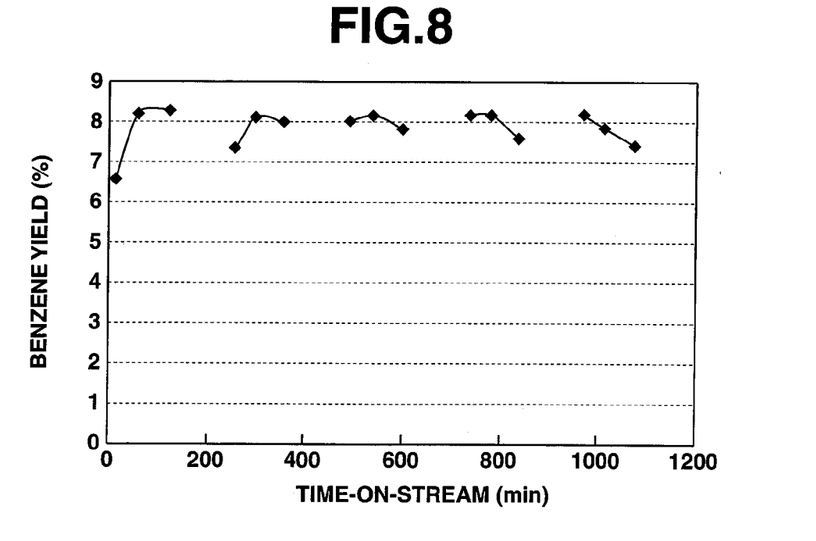
FIG. 8 is a graph showing a time-based change of a benzene yield in the first reactor, obtained when the catalytic reaction and the regeneration reaction are repeated in the aromatic hydrocarbon producing system according to the second embodiment of the present invention.
Figure 9:
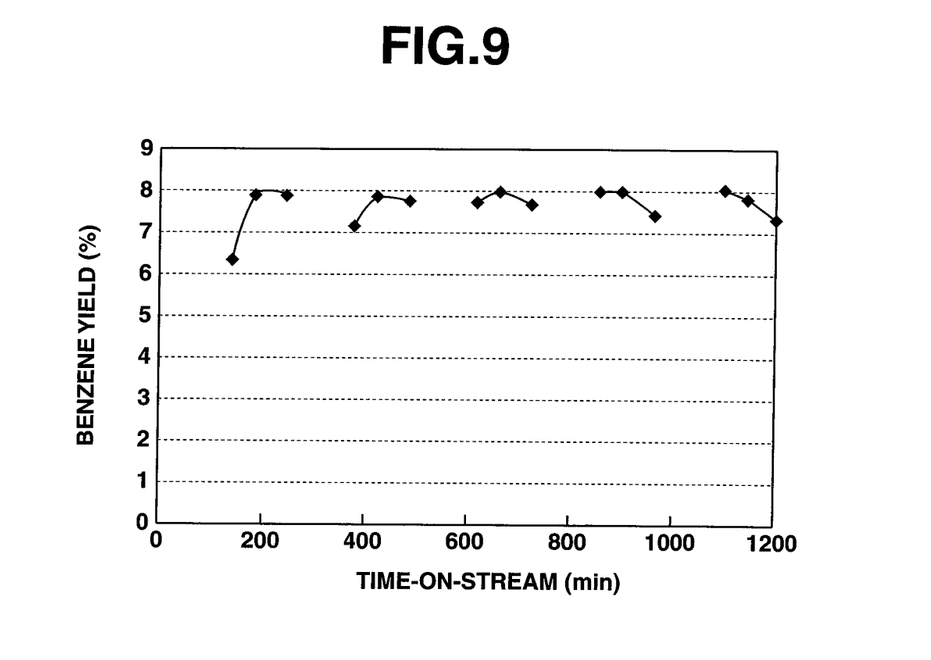
FIG. 9 is a graph showing a time-based change of a benzene yield in the second reactor, obtained when the catalytic reaction and the regeneration reaction are repeated in the aromatic hydrocarbon producing system according to the second embodiment of the present invention.
Figure 10:
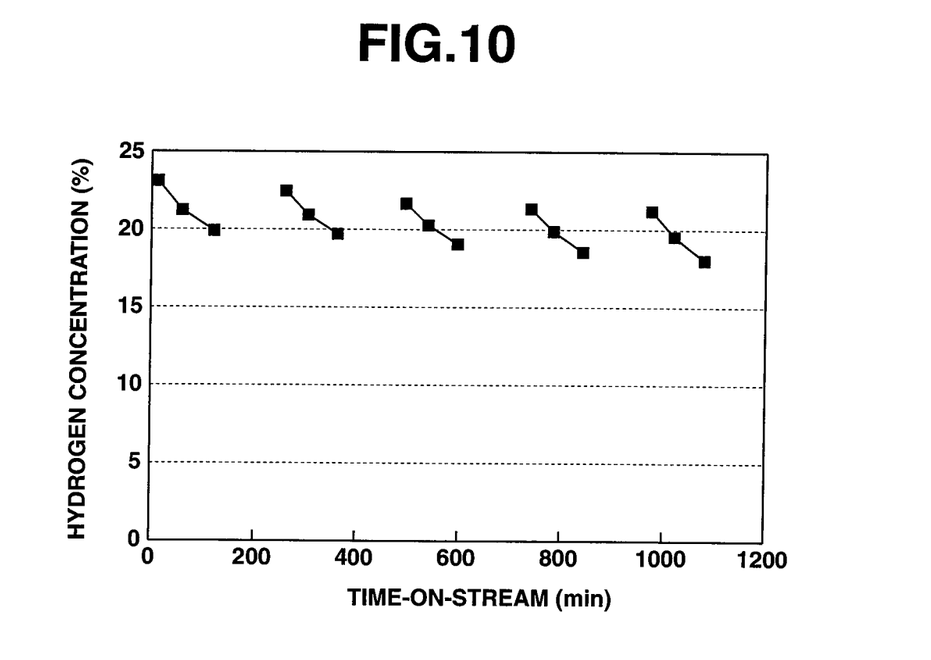
FIG. 10 is a graph showing a time-based change of a hydrogen concentration in off-gas in the first reactor 1, obtained when aromatic hydrocarbon is produced in the aromatic hydrocarbon producing system according to the second embodiment of the present invention.

FIGS. 8 to 10 show analysis results of a benzene yield and a hydrogen concentration obtained when aromatic hydrocarbon was produced in the aromatic hydrocarbon producing system 12.

Upon comparison between FIG. 8 and FIG. 9, it will be understood that aromatic hydrocarbon can be continuously produced maintaining a catalytic activity by alternately repeating the catalytic reaction and the regeneration reaction in each of the first reactor 1 and the second reactor 2.

As shown in FIG. 10, the hydrogen concentration in the off-gas in the first reactor 1 is not lower than 15% and not higher than 25% similarly to in the first embodiment.

As described in the comparative example discussed with reference to FIGS. 4 to 6, if the hydrogen concentration in the off-gas is lower than 15%, the benzene yield is low, and the deterioration of the catalyst proceeds while forming a corking section which cannot be removed.

Additionally, in the first and second embodiments of the present invention, the off-gas is used has the regeneration gas, so that it is apparent that a regeneration ability is lowered if the hydrogen concentration in the off-gas lowers.

The standard for changing over the reaction step to the regeneration step is preferably the hydrogen concentration of not lower than 15% for the above-discussed two reasons. In other words, if the hydrogen content is lower than 15%, the deterioration of the catalyst excessively proceeds while the hydrogen content in the regeneration gas used in the regeneration is low thereby making it difficult to repeat the regeneration reaction.

The present invention is not limited to the examples, so that reaction conditions, catalysts (kinds and amounts of metals carried thereon), and the like may be suitably selectable.

EXPLANATION OF REFERENCE NUMERALS

1 . . . first reactor
2 . . . second reactor
3 . . . aromatic hydrocarbon separation apparatus
4 . . . hydrogen monitor
10, 11, 12 . . . aromatic hydrocarbon producing system

The invention claimed is:

1. A method of producing aromatic hydrocarbon, comprising:

alternately repeating a reaction step for obtaining aromatic hydrocarbon upon making a contact reaction between a lower hydrocarbon comprising methane, ethane, or propane and a catalyst, and a regeneration step for regenerating the catalyst used in the reaction step, wherein off-gas, which consists of only gas obtained by removing aromatic hydrocarbon produced in the reaction step from discharge gas passing through the reaction step, is used as a regeneration gas in the regeneration step, and wherein a hydrogen concentration in the off-gas is in a range of 20 to 25 vol %.

2. The method of producing aromatic hydrocarbon as claimed in claim 1, wherein the reaction step is changed over into the regeneration step, based on the hydrogen concentration in the off-gas.

3. The method for producing aromatic hydrocarbon as claimed in claim 1, wherein after the reaction step, the discharge gas is discharged from a reactor and supplied to an aromatic hydrocarbon separation apparatus that separates the aromatic hydrocarbon produced in the reactor from the discharge gas to obtain the off-gas, and the off-gas is stored in an off-gas tank that supplies the off-gas, as it is, to the reactor to initiate the regeneration step.

* * * * *